United States Patent [19]
Allen et al.

[11] Patent Number: 5,654,151
[45] Date of Patent: Aug. 5, 1997

[54] HIGH AFFINITY HIV NUCLEOCAPSID NUCLEIC ACID LIGANDS

[75] Inventors: Patrick Nikita Allen; Larry Gold, both of Boulder, Colo.

[73] Assignee: NeXstar Pharmaceuticals, Inc., Boulder, Colo.

[21] Appl. No.: 477,830

[22] Filed: Jun. 7, 1995

Related U.S. Application Data

[63] Continuation-in-part of Ser. No. 714,131, Jun. 10, 1991, Pat. No. 5,475,096, Ser. No. 931,473, Aug. 17, 1992, Pat. No. 5,270,163, Ser. No. 964,624, Oct. 21, 1992, Pat. No. 5,496,938, Ser. No. 117,991, Sep. 8, 1993, abandoned, Ser. No. 361,795, Dec. 21, 1994, and Ser. No. 447,172, May 19, 1995, said Ser. No. 714,131, is a continuation-in-part of Ser. No. 536,428, Jun. 11, 1990, abandoned.

[51] Int. Cl.$^6$ .............................. C12P 19/34; C12Q 1/68
[52] U.S. Cl. ................... 435/6; 435/91.2; 536/23.1; 935/77; 935/78
[58] Field of Search .................. 435/6, 91.2; 536/23.1; 935/77, 78

[56] References Cited

U.S. PATENT DOCUMENTS 5,475,096  12/1995  Gold et al. ..................... 536/22.1

FOREIGN PATENT DOCUMENTS

| 2 183 661 | 6/1987 | United Kingdom . |
| WO 89/06694 | 7/1989 | WIPO . |
| 9214843 | 9/1992 | WIPO ........................... 435/6 |

OTHER PUBLICATIONS

Joyce (1989) Gene 82:83.
Joyce and Inoue (1989) Nucleic Acids Research 17:711.
Ellington and Szostak (1990) Abstract of papers presented at the 1990 meeting on RNA processing, Cold Spring Harbor Laboratory, Cold Spring Harbor, NY, p. 226.
Kinzler and Vogelstein (1989) Nucleic Acids Research 17:3645.
Kramer et al. (1974) J. Mol. Biol. 89:719.
Levisohn and Spiegelman (1969) Proc. Natl. Acad. Sci. USA 63:805.
Levisohn and Spiegelman (1968) Proc. Natl. Acad. Sci. USA 60:866.
Oliphant et al. (1989) Mol. Cell. Biol. 9:2944.
Oliphant and Struhl (1988) Nucleic Acids Research 16:7673.
Oliphant and Struhl (1987) Methods in Enzymology 155:568.
Oliphant et al. (1986) Gene 44:177.
Robertson and Joyce (1990) Nature 344:467.
Thiesen and Bach (1990) Nucleic Acids Research 18:3203.
Rice et al. (1993) Proc. Natl. Acad. Sci. USA 90:9721.
Tanchou et al. (1994) Aids Research and Human Retroviruses 10:983.

*Primary Examiner*—Stephanie W. Zitomer
*Attorney, Agent, or Firm*—Swanson & Bratschun LLC

[57] ABSTRACT

Methods are described for the identification and preparation of high-affinity nucleic acid ligands to HIV-1 nucleocapsid. Included in the invention are specific RNA ligands to HIV-1 nucleocapsid identified by the SELEX method. Also included are RNA ligands that inhibit the function of HIV-1 nucleocapsid.

8 Claims, No Drawings

HIGH AFFINITY HIV NUCLEOCAPSID NUCLEIC ACID LIGANDS

RELATED APPLICATIONS

This application is a continuation in part of U.S. patent application Ser. No. 07/714,131, filed Jun. 10, 1991, entitled Nucleic Acid Ligands now issued as U.S. Pat. No. 5,475,096, U.S. patent application Ser. No. 07/931,473, filed Aug. 17, 1992, entitled Nucleic Acid Ligands, now issued as U.S. Pat. No. 5,270,163, U.S. patent application Ser. No. 07/964,624, filed Oct. 21, 1992, entitled Nucleic Acid Ligands to HIV-RT and HIV-Rev now issued as U.S. Pat. No. 5,496,938, U.S. patent application Ser. No. 08/117,991, filed Sep. 8, 1993, entitled High-Affinity Nucleic Acid Ligands Containing Modified Nucleotides now abandoned, U.S. patent application Ser. No. 08/361,795, entitled High Affinity HIV Integrase inhibitors, filed Dec. 21, 1994, and U.S. patent application Ser. No. 08/447,172 entitled High Affinity HIV-1 GAG Nucleic Acid Ligands, filed May 19, 1995. U.S. patent application Ser. No. 07/714,131 now issued as U.S. Pat. No. 5,475,096 is a continuation in part of U.S. patent application Ser. No. 07/536,428, filed Jun. 11, 1990, entitled Systematic Evolution of Ligands by EXponential Enrichment, now abandoned.

This work was partially supported by grants from the United States Government funded through the National Institutes of Health (Grant Nos. GM28685, GM19963, and AI-33380). The U.S. Government may have certain rights in this invention. This work was also supported in part by the Jane Coffin Childs Memorial Fund.

FIELD OF THE INVENTION

Described herein are methods for identifying and preparing high-affinity nucleic acid ligands to HIV-1 nucleocapsid. The method utilized herein for identifying such nucleic acid ligands is called SELEX, an acronym for Systematic Evolution of Ligands by EXponential enrichment. This invention includes high affinity nucleic acid ligands of HIV-1 nucleocapsid. Further disclosed are RNA ligands to HIV-1 nucleocapsid. The invention includes high-affinity RNA inhibitors of HIV-1 nucleocapsid. The oligonucleotides of the present invention are useful as pharmaceuticals or diagnostic agents.

BACKGROUND OF THE INVENTION

One of the first events during the replication of HIV-1 and all other known retroviruses is conversion of genomic RNA to DNA using the viral reverse transcriptase (RT) and other host cell components (for review see Coffin, 1982; Varmus and Brown, 1989; Wain-Hobson, 1994). The viral RNA is reverse transcribed by RT with a host tRNA being used as the primer (reviewed in Wong-Staal, 1990; Vaishnav and Wong-Staal, 1991). Nucleocapsid protein plays an instrumental role in annealing of the primer to the genomic RNA. It has been suggested that nucleocapsid from Mason-Pfizer monkey virus (MPMV) and HIV-1 stimulates annealing of tRNA primer to viral RNA by over two orders of magnitude (Dib-Hajj et al., 1993). Moreover, it has been shown that the nucleocapsid proteins of Rous sarcoma virus (RSV) and murine leukemia virus(MuLV) are directly involved in annealing the tRNA primer onto the primer binding site under physiological conditions (Prats et al., 1988; Barat et al., 1989). In addition, nucleocapsid has been implicated in dimer formation of genomic RNA (Kung et al., 1976; Meric and Spahr, 1986; Prats et al., 1988; Bieth et al., 1990), non-specific coating of the viral RNA genome (Fleissnerand Tress, 1973; Chen et al., 1980), encapsidation of full-length genomic RNA (South and Summers, 1993) and interaction with RT during reverse transcription suggesting it may play a role in template transfer (Panganiban and Fiore, 1988; Barat et al. 1989).

Retroviral nucleocapsid proteins are gag precursor products (Mervis et al., 1988; Morellet et al., 1992). HIV-1 nucleocapsid protein contains two zinc finger binding domains with the following general structure Cys-$X_2$-Cys-$X_4$-His-$X_4$-Cys (SEQ ID NO: 26) (Gorelick et al., 1993). Mutations in each of these finger domains result in different functional and structural defects (Gorelick et al., 1990; Gorelick et. al., 1993; Julian et al., 1993). Similar types of mutations in RSV and MuLV nucleocapsid-proteins resulted in defects in RNA packaging and dimer formation (Meric and Spahr, 1986; Meric and Goff, 1989). Results from these studies suggested a role for nucleocapsid during reverse transcription (Meric and Goff, 1989; Weiss et al., 1992) and possibly during infection (Meric and Spahr, 1986). Other mutational studies demonstrated that substitutions of the conserved Cys residues in the Zn++ finger domain perturb sequence specific binding by nucleocapsid (Delahunty et al., 1992).

Sequences near the 5' end of the mature HIV-1 viral RNA are involved in encapsidation (Aldovini and Young, 1990). It appears these sequences interact specifically with the nucleic acid binding zinc finger domains of HIV-1 nucleocapsid (NC). Mutations in either of the two Zn++ fingers or the encapsidation site resulted in similar defects. The 5' end of retroviral RNAs have been rigorously studied and thus the structural and functional characterization is extensive (Bender et al., 1978; Murti et al., 1981; Darlix et al., 1982; Aldovini and Young, 1990; Harrison and Lever, 1992; Surovoy et al., 1993).

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands now issued as U.S. Pat. No. 5,475,096," U.S. patent application Ser. No. 07/931,473, filed Aug. 17, 1992, entitled "Nucleic Acid Ligands," now U.S. Pat. No. 5,270,163 (see also PCT/US91/04078), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure" now abandoned, describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" now abandoned describes a SELEX based method for selecting nucleic acid ligands containing photoreactive groups capable of binding and/or photocrosslinking to and/ or photoinactivating a target molecule. U.S. patent application Ser. No. 08/134,028, filed Oct. 7, 1993, entitled "High-Affinity Nucleic Acid Ligands That Discriminate Between Theophylline and Caffeine," now abandoned describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," now abandoned describes a SELEX-based method which achieves highly efficient partitioning between oligonucleotides having high and low. affinity for a target molecule. U.S. patent application Ser. No. 07/964,624, filed Oct. 21, 1992, entitled Nucleic Acid Ligands to HIV-RT and HIV-1 Rev now issued as U.S. Pat. No. 5,496,938 describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides" now abandoned, that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-NH$_2$), 2'-fluoro (2'-F), and/or 2'-O-methyl (2'-OMe). U.S. patent application Ser. No. 08/264,029, filed Jun. 22, 1994, entitled "Novel Method of Preparation of known and novel 2' Modified nucleosides by Intramolecular Nucleophilic Displacement," describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX" and U.S. patent application Ser. No. 08/234,997, filed Apr. 28, 1994, entitled "Systematic Evolution of Ligands by Exponential Enrichment: Blended SELEX," respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

Parent U.S. patent application Ser. No. 08/447,172 (Express Mail Receipt No. TB865017604US), entitled High Affinity HIV-1 GAG Nucleic Acid Ligands, filed May 19, 1995, which is hereby incorporated by reference in its entirety, describes a method for identifying nucleic acid ligands to HIV-1 GAG polyprotein, and the nucleic acids so produced. Nucleocapsid is a component of the GAG polyprotein.

HIV-1 nucleocapsid is an attractive target for the development of SELEX ligands because HIV-1 nucleocapsid plays such a crucial role in so many different viral processes.

The development of high affinity ligands capable of inhibiting HIV-1 nucleocapsid would be useful in the treatment of Human Immunodeficiency Virus. Herein described are high affinity RNA ligand inhibitors of HIV-1 nucleocapsid.

BRIEF SUMMARY OF THE INVENTION

The present invention includes methods of identifying and producing nucleic acid ligands to nucleocapsid proteins, and the nucleic acid ligands so identified and produced. Specifically included are a method of identifying and producing nucleic acid ligands to Human Immunodeficiency Virus 1 nucleocapsid (HIV-1 nucleocapsid), and homologous nucleocapsids, and the nucleic acid ligands so identified and produced. In particular, RNA sequences are provided that are capable of binding specifically to HIV-1 nucleocapsid. Specifically included in the invention are the RNA ligand sequences shown in Table 2 (SEQ ID NOS: 4–25).

Also included in this invention are RNA ligands of HIV-1 nucleocapsid that are inhibitors of HIV-1 nucleocapsid. Specifically, RNA ligands are identified and described which inhibit the function of HIV-1, presumably by inhibiting the annealing activity of nucleocapsid. Further included in this invention is a method of identifying nucleic acid ligands and nucleic acid ligand sequences to HIV-1 nucleocapsid comprising the steps of (a) preparing a candidate mixture of nucleic acids, (b) contacting the candidate mixture of nucleic acids with HIV-1 nucleocapsid, (c) partitioning between members of said candidate mixture on the basis of affinity to HIV-1 nucleocapsid, and (d) amplifying the selected molecules to yield a mixture of nucleic acids enriched for nucleic acid sequences with a relatively higher affinity for binding to HIV-1 nucleocapsid.

Also included in the invention is the method of identifying nucleic acid ligands and ligand sequences described above wherein the mixture contacted includes non-amplifiable random pool nucleic acids.

More specifically, the present invention includes the RNA ligands to HIV-1 nucleocapsid identified according to the above-described method, including those ligands shown in Table 2 (SEQ ID NOS: 4–25). Also included are RNA ligands to HIV-1 nucleocapsid that are substantially homologous to any of the given ligands and that have substantially the same ability to bind HIV-1 nucleocapsid and inhibit the function of HIV-1 nucleocapsid. Further included in this invention are nucleic acid ligands to HIV-1 nucleocapsid that have substantially the same structural form as the ligands presented herein and that have substantially the same ability to bind HIV-1 nucleocapsid and inhibit the function of HIV-1 nucleocapsid.

The present invention also includes modified nucleotide sequences based on the RNA ligands identified herein and mixtures of the same.

DETAILED DESCRIPTION OF THE INVENTION

This application describes high-affinity nucleic acid ligands to HIV-1 nucleocapsid identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands now issued as U.S. Pat. No. 5,474,096, U.S. patent application Ser. No. 07/931,473, filed Aug. 17, 1992, entitled Nucleic Acid Ligands, now U.S. Pat. No. 5,270,163, (see also PCT/US91/04078). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The methods described herein and the nucleic acid ligands identified by such methods are useful for both therapeutic and diagnostic purposes. Therapeutic uses include the treatment or prevention of diseases or medical conditions in human patients. Diagnostic utilization may include both in vivo or in vitro diagnostic applications. The SELEX method generally, and the specific adaptations of the SELEX method taught and claimed herein specifically, are particularly suited for diagnostic applications. SELEX identifies nucleic acid ligands that are able to bind targets with high affinity and with surprising specificity. These characteristics are, of course, the desired properties one skilled in the art would seek in a diagnostic ligand.

The nucleic acid ligands of the present invention may be routinely adapted for diagnostic purposes according to any number of techniques employed by those skilled in the art. Diagnostic agents need only be able to allow the user to identify the presence of a given target at a particular locale or concentration. Simply the ability to form binding pairs with the target may be sufficient to trigger a positive signal for diagnostic purposes. Those skilled in the art would also be able to adapt any nucleic acid ligand by procedures known in the art to incorporate a labeling tag in order to track the presence of such ligand. Such a tag could be used in a number of diagnostic procedures. The nucleic acid ligands to HIV-1 nucleocapsid described herein may specifically be used for identification of HIV-1 nucleocapsid.

SELEX provides high affinity ligands of a target molecule. This represents a singular achievement that is unprecedented in the field of nucleic acids research. The present invention applies the SELEX procedure to the specific target of HIV-1 nucleocapsid. In the Example section below, the experimental parameters used to isolate and identify the nucleic acid ligands to HIV-1 nucleocapsid are described.

In order to produce nucleic acids desirable for use as a pharmaceutical, it is preferred that the nucleic acid ligand (1) binds to the target in a manner capable of achieving the desired effect on the target; (2) be as small as possible to obtain the desired effect; (3) be as stable as possible; and (4) be a specific ligand to the chosen target. In most situations, it is preferred that the nucleic acid ligand have the highest possible affinity to the target.

In commonly assigned U.S. patent application Ser. No. 07/964,624, filed Oct. 21, 1992 ('624) now issued as U.S. Pat. No. 5,496,938, methods are described for obtaining improved nucleic acid ligands after SELEX has been performed. The '624 application, entitled Methods of Producing Nucleic Acid Ligands, is specifically incorporated herein by reference.

This application is a continuation in part application of U.S. patent application Ser. No. 08/447,172, entitled High Affinity HIV-1 GAG Nucleic Acid Ligands, filed May 19, 1995. The nucleic acid ligands identified to the HIV-1 GAG polyprotein may be identical to the nucleic acid ligand sequences identified to HIV-1 nucleocapsid.

In the present invention, a SELEX experiment was performed in order to identify RNA with specific high affinity for HIV-1 nucleocapsid from a degenerate library containing 30 random positions (30N) (Examples 1 and 2). Secondary structure of selected ligands was predicted by computer analysis (Example 3). Boundary analysis and RNA truncate studies of a selected ligand were performed to determine the minimal binding domain of the RNA (Example 4). In vitro inhibition of nucleocapsid is demonstrated in Example 5. Nucleocapsid footprints on the RNA show that different parts of the RNA are shielded from digestion by S1 nuclease (Example 6). Modified 2'-NH$_2$ pyrimidine RNA ligands to HIV-1 nucleocapsid are described in Example 7.

This invention includes the specific RNA ligands to HIV-1 nucleocapsid shown in Table 2 (SEQ ID NOS: 4–25), identified by the method described in Examples 1–2. The scope of the ligands covered by this invention extends to all nucleic acid ligands of HIV-1 nucleocapsid, modified and unmodified, identified according to the SELEX procedure. More specifically, this invention includes nucleic acid sequences that are substantially homologous to the RNA ligands shown in Table 2 (SEQ ID NOS: 4–25). By substantially homologous it is meant a degree of primary sequence homology in excess of 70%, most preferably in excess of 80%. Sequences with little or no primary homology may have substantially the same ability to bind HIV-1 nucleocapsid. For these reasons, this invention also includes nucleic acid ligands that have substantially the same ability to bind HIV-1 nucleocapsid as the nucleic acid ligands shown in Table 2 (SEQ ID NOS: 4–25). Substantially the same ability to bind HIV-1 nucleocapsid means that the affinity is within one to two orders of magnitude of the affinity of the ligands described herein. It is well within the skill of those of ordinary skill in the art to determine whether a given sequence—substantially homologous to those specifically described herein—has substantially the same ability to bind HIV-1 nucleocapsid.

This invention also includes the ligands as described above, wherein certain chemical modifications are made in order to increase the in vivo stability of the ligand or to enhance or mediate the delivery of the ligand. Examples of such modifications include chemical substitutions at the ribose and/or phosphate and/or base positions of a given nucleic acid sequence. See, e.g., Cook et al. PCT Application WO 92/03568; U.S. Pat. No. 5,118,672 of Schinazi et al.; Hobbs et al. (1973) Biochem. 12:5138; Guschlbauer et al. (1977) Nucleic Acids Res. 4:1933; Shibahara et al.; (1987) Nucleic Acids Res. 15:4403; Pieken et al. (1991) Science 253:314, each of which is specifically incorporated herein by reference. Such modifications may be made post-SELEX (modification of previously identified unmodified ligands) or by incorporation into the SELEX process.

The RNA ligands to HIV-1 nucleocapsid described herein are useful as pharmaceuticals. This invention, therefore, also includes a method for the treatment of HIV-1 by administration of a nucleic acid ligand capable of binding to the HIV-1 nucleocapsid.

Therapeutic compositions of the RNA ligands may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parenteral administration in either unit dose or multi-dose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing RNA ligands for systemic delivery may be via subcutaneous, intramuscular, intravenous, intranasal or vaginal or rectal suppository.

The following examples are provided to explain and illustrate the present invention and are not to be taken as limiting of the invention.

EXAMPLE 1

EXPERIMENTAL PROCEDURES

This Example provides general procedures followed and incorporated into the specific Examples that follow.
Materials.

HIV-1 capsid-nucleocapsid (CA-NC) and nucleocapsid, isolated from pBH10, were generous gifts of Agouron Pharmaceutical Inc., 3565 General Atomics Court, San Diego, Calif. 92121-1121. The BH10 clone is also publicly available from the AIDS Reagent Program, 685 Loftstrand Lane, Rockville, Md. 20850. Isolating and purifying HIV-1 capsid and nucleocapsid from BH10 would be routine for those skilled in the art. DNA polymerase was purchased from Perkin Elmer Cetus. Alkaline Phosphatase (Calf Intestinal) was purchased from Biolabs. T4 polynucleotide kinase was purchased from Boehringer. Cobra Venom Ribonuclease ($V_1$) was purchased from Pharmacia, and Ribonuclease $T_1$ was purchased from Boehringer. All other enzymes were purchased from commercial sources. pUC18 was purchased from BRL.
PCR Amplification and Selection.

SELEX was carried out essentially as described in the SELEX Patent Applications (see also Tuerk and Gold (1990) Science 249:505–510). A random pool of DNA $10^{14}$ oligomers was synthesized where the 5' and 3' proximal ends were fixed sequences used for amplification and the central regions consisted of 30 randomized positions (see Table 1 for the starting ssDNA template (SEQ ID NO: 1), the 3' PCR primer (SEQ ID NO:2) and the 5' PCR primer (SEQ ID NO:3). Five picomoles of a random pool of DNA oligomers were used as template for PCR amplification for 8 cycles in the initial round. Copy DNA of the selected pool of RNA from subsequent rounds of SELEX was PCR amplified 18 cycles. PCR reactions were carried out in 50 µl volume containing 200 picomoles of each primer, 2 mM final concentration dNTP's, 5 units of Thermus aquaticus DNA polymerase (Perkin Elmer Cetus) in a PCR buffer (10 mM Tris-Cl pH 8.4, 50 mM KCl, 7.5 mM MgCl$_2$, 0.05 mg/ml BSA). Primers were annealed at 58° C. for 20 seconds and extended at 74° C. for 2 minutes. Denaturation occurred at 93° C. for 30 seconds.

PCR products were transcribed using T7 RNA polymerase in vitro in a 200 µl reaction volume (Tuerk and Gold, 1990). T7 transcripts were purified from a 6 percent, 7M Urea polyacrylamide gel and eluted by crushing gel pieces in a Sodium Acetate/EDTA solution. For each round of SELEX, 50 picomoles of the selected pool of RNA is phosphatased using Alkaline Phosphatase, Calf Intestinal (Biolabs) and 25 picomoles was 5' end-labeled using $\gamma$-$^{32}$P ATP with polynucleotide kinase (Boehringer) for 30 minutes. Kinased RNA was gel purified and about 150,000 cpm was used to follow the fraction of RNA bound to nucleocapsid and retained on nitrocellulose filters during selection.

Typically a protein concentration was used that binds one to five percent of the total input RNA. A control (minus protein) was used to determine the background which is typically $\leq 0.1\%$ of the total input. Selected RNA was eluted from filter by extracting three times with H$_2$O saturated phenol containing 2% lauryl sulfate (SDS), 0.3M NaOAc and 5 mM EDTA followed by a chloroform extraction. Twenty five percent of this RNA was then used to synthesize cDNA for PCR amplification.

Selection with non-amplifiable Competitor RNA.

Competitor-RNA SELEX was carried out as described below (see also U.S. patent application Ser. No. 08/361,795, entitled High Affinity HIV Integrase Inhibitors, filed Dec. 21, 1994, which is incorporated by reference in its entirety herein). Selections were done using two buffer conditions where the only difference between the buffers is the concentration of NaCl (Buffer A: 10 mM NaOAc (pH 5.3), 2 mM 2-mercaptoethanol, 0.1 mM ZnCl$_2$, 5 mM MgCl$_2$, 200 mM NaCl; Buffer B: 10 mM NaOAc (pH 5.3), 2 mM 2-mercaptoethanol, 0.1 mM ZnCl$_2$, 5 mM MgCl$_2$, 400 mM NaCl). Two different buffer conditions were used to increase stringency (with the higher salt concentration being more stringent) and to determine whether different ligands would be obtained. 500 pmoles of the parent pool of RNA were used in the first round of selection along with about 100 fmoles $\gamma$-labeled RNA from the same pool. RNA was recovered and cDNA synthesized and PcR amplified. In rounds 2 through 8, 250 pmoles of the selected RNA were used with labeled RNA from that pool to follow the amount of recovery. In each round, other than round 1, about 3% of the total input RNA was selected or a smaller fraction if counts were greater than ten fold above the control. For rounds 9 and 10, the amount of Riga was reduced to 25 pmoles. During the last 7 rounds, (rounds 11–17), selection was carried out in the presence and absence of competitor RNA. 25 pmoles of cold selected RNA was used and 500 pmoles of a random pool of competitor RNA as described in U.S. patent application Ser. No. 08/361,795, entitled High Affinity HIV Integrase Inhibitors, filed Dec. 21, 1994, which is incorporated by reference in its entirety herein, (see also Allen et al., 1995).

For rounds 10 through 16, a 50-fold excess of a non-amplifiable random pool of RNA was present during selection to compete with non-specific low-affinity binders that may survive and thus be amplified. The competitor RNA, which has a (30N) random region, was made as described supra for the amplifiable pool RNA; however, the competitor RNA had different primer annealing sequences (3' PCR primer, RNA reverse transcription primer: CCCGGATC-CTCTTTACCTCTGTGTG (SEQ ID NO:27); 5' PCR primer, T7 promoter: CCGAAGCTTAATACGACTCAC-TATAGGGACTATTGATGGCCTTCCGACC (SEQ ID NO:28). Thus, the competitor RNA does not survive the cDNA synthesis or PCR amplification steps. It would be apparent to one skilled in the art that other primer sequences could be used as long as they were not homologous to those used for the pool RNA.

Cloning and Sequencing

PCR amplified DNA from round 16 selected-pool of RNA was phenol and chloroform extracted and ethanol precipitated. The extracted PCR DNA was digested using Bam HI and Hind III (Biolabs) and subcloned into pUC18. Ligation was carried out at room temperature for two hours after which time the reaction was phenol and chloroform extracted and used to electroporate competent cells. Twenty-five transformants from the SELEX done in the low salt buffer and thirty from the high salt experiment were picked and their DNAs sequenced.

Chemical and Enzymatic Modification of Selected RNAs

RNAS were chemically modified using CMCT (1-Cyclohexyl-3-(2-Morpholinoethyl)-Carbodiimide Metho-p-Toluene-sulfonate), kethoxal (2-keto, 3-ethoxy-n-butyraldehyde) and DMS (dimethyl sulfate) as described (Allen and Noller, 1989) with a few exceptions. RNA was preincubated for 5 minutes at 45° C., 8 minutes at 37° C. with reagents in modification buffer (80 mM potassium borate (pH 8), 10 mM magnesium chloride, and 100 mM sodium chloride). In addition, RNAs were partially digested using ribonuclease S1 (0.2 units/reaction), T1 (0.2 units/reaction), cobra venom V1 (0.03 units/reaction) and chicken liver nuclease CL3 (1 unit/reaction). Each modification reaction that was carried out in the absence of nucleocapsid protein contained 15 picomoles of RNA (approximately 0.38 µg). Where chemical modification or enzymatic digestion is carried out with NC present in the reaction mixture, the concentration varied from 0.05 µM to 10 µM and the amount of RNA used was 4 pmol per reaction. Nucleocapsid and RNA was incubated together in binding buffer at 37° C. for 20 minutes then transferred to ice for 5 minutes before adding RNase for an additional 5 minutes. The stock of RNases was also preincubated at 4° C. before adding to reactions. The mix was phenol extracted three times, chloroform extracted twice and then ethanol precipitated and stored at –20° C. Primer extensions (Stern et al., 1988) were done the day of nuclease treatment to identify positions that are accessible to the probes and enzymes. The method of footprinting of the various affinity binding sites was essentially carried out as described (McPheeters et al., 1988).

Binding Assays

Binding assays were done by adding 5 µl of HIV-1 p7 nucleocapsid protein, at the appropriate concentrations (i.e., ranging from $6\times10^{-10}$ to $5\times10^{-8}$), to 45 µl of binding buffer (10 mM NaOAc (pH 5.3), 2 mM 2-mercaptoethanol, 0.1 mM ZnCl$_2$, 5 mM MgCl$_2$, 100 mM NaCl) on ice, then adding 80,000 cpm of kinased RNA (<200 fmoles) in a volume of 3 to 4 µl. This mix was incubated at 37° C. for 20 minutes. The reactions were then passed over nitrocellulose filters, which were pre-equilibrated in the same buffer, and washed five times with one milliliter each time using a 50 mM Tris-Cl pH 7.5 solution. Filters were dried and counted in cocktail. The protein used in these experiments were frozen and thawed only once. Each binding curve consisted of seven points and each point is the average of duplicates.

Determination of Minimum Binding Domain

Boundary determination experiments were carried out essentially as previously published (Tuerk et al., 1990) with the following exceptions. The transcripts were treated with alkaline phosphatase, calf intestinal (Biolabs). For each reaction, 25 picomoles of partially hydrolyzed RNA was incubated with nucleocapsid protein in binding buffer in a final reaction volume of 50 µl. Nucleocapsid concentrations were $0.5\times10^{-9}$, $1\times10^{-9}$ and $5\times10^{-9}$ in each case. Reactions were quenched as previously described (Chen and Gold, 1994). Transcripts retained on filters were eluted using 150 µl of 1% SDS/0.3M NaOAc/1 mM EDTA solution, phenol extracted twice, chloroform extracted and then precipitated with ethanol.

In Vitro Inhibition Assay

The 5' end of a synthetic DNA oligonucleotide Con(+) (5'-CAATGACCGCATGGGATCCGTGTGGAAAAT-CTCTAGCAGT-3') (SEQ ID NO: 29) was labeled with $\gamma$-$^{32}$P ATP using polynucleotide kinase (Boehringer). 10 nM labeled con+ was incubated at 37° C. with equal molar ratio of the complementary strand con(−) (5'-ACTGCTAGAGATTTTCCACACGGATCCCATGCGGT-CATTG-3') (the complement of SEQ ID NO: 29) in binding buffer (above) containing no NaCl or increasing concentrations of NaCl for 6 minutes and then run on a 8% native acrylamide gel to determine the salt concentration that gives approximately 50% duplex. Binding buffer containing 200 mM NaCl converted 40 to 70 percent labeled con+ to duplex. This buffer was used and the concentration of each oligo was reduced keeping their action time constant to find an oligo concentration that would give less than 10% duplex formation under these conditions. The conditions in the reaction used for inhibition assay was as follows. 400 pM each DNA oligo (con±) was mixed with 10 nM nucleocapsid for 6 minutes at 37° C. in binding buffer containing 200 mM NaCl in a reaction volume of 30 µl. After this time, reactions were stopped by placing on ice and loaded on gel after 2 minutes. Gels were run at 250 volts for 3.5 hours. In reactions where random RNA was added as inhibitor, the concentrations range from 6500 nM to 9 nM. Where selected PaNAs were used, the range was 720 nM to 0.11 nM.

Synthesis of RNA Truncates

Truncates of 400-23 RNA were made by using primers that anneal approximately 10 nucleotide increments from the 3' end of the RNA to synthesize cDNAs. Primers and RNAs were heated to 90° C. and cooled slowly to 45° C. to anneal and primer extension was carried out at 48° C. cDNAs were then PCR amplified using the same 3' primers with the original 5' primer and used to transcribe RNAs in vitro that were truncated at their 3' ends. In addition to in vitro transcriptions, the shortest truncate (T-23) was also made synthetically. Truncates were then used in binding studies as described above.

EXAMPLE 2

SEQUENCE ANALYSIS

Sequencing a total of 55 clones isolated after 16 complete rounds of SELEX resulted in multiple copies of 14 distinct sequences. Each sequence encodes a fourteen nucleotide block which is nearly identical. This highly conserved fourteen-base sequence-block occurs at different positions within the region which was randomized. Six of the isolates have single-base substitutions within the 14 nucleotide sequence-block. This highly conserved fourteen-base sequence-block occurs at different positions within the region which was randomized. The single base changes within the conserved sequence-block occur at the ninth and fourteenth positions (Table 2). Five of the 55 isolates have a single base substitution U to A at the 9$^{th}$ position in this block. One other clone has a C to U base change at the last position in the block. All other positions in this conserved block in all other clones are identical. Besides the conserved sequence-block there is no other sequence homology shared among these selected sequences with the exception of a highly conserved cytosine at the last position of the random region. However, the sequences 3' of the conserved block are very uridine rich while the 5' sequences are adenine rich. In general, the conserved sequence is located proximal to the 5' end of the random region. There is nearly equal representation among the different sequences within the selected pool. This is consistent with the fact that all the clones tested had very similar dissociation constants. Thus, the apparent heterogeneity of sequences flanking the conserved fourteen nucleotides may not be important for binding specificity.

Filter Binding Studies

The dissociation constants for 12 of the 14 RNA species were determined by nitrocellulose filter binding. These experiments were carried out in duplicates. All binding curves were done using $\gamma$-$^{32}$P labeled RNA in binding buffer containing 100 mM NaCl. Binding affinities range from $2\times10^{-9}$ to $6\times10^{-9}$ molar for these RNAs (data not shown). The affinity of the two selected pools of RNA for nucleocapsid protein was on the same order. The $K_d$ for the initial random pool of RNA in the same buffer could not be determined since there was no significant binding above background at the highest protein concentration ($10^{-7}$M). Binding affinities were determined for 6 of the 12 isolates (3 from each of the SELEX experiments in which two buffer conditions were used) for a precursor fusion protein derived from HIV-1 gag region (CA-NC; Capsid (p24) fused to Nucleocapsid (p7)). The 322 amino acid polypeptide product, which encodes the entire 55 amino acid sequence of the NC used in the SELEX experiments, had no detectable binding affinity for these RNAs (data not shown). This was a demonstration of the specificity of the ligands for nucleocapsid and suggests that the conformation of the nucleocapsid domain within the gag precursor is different from the processed NC and these ligands probably would serve only as inhibitors for processed nucleocapsid.

EXAMPLE 3

PREDICTED SECONDARY STRUCTURE OF SELECTED LIGANDS

RNA Structure Analysis

RNA Structure Analysis RNA transcripts were sequenced directly and entered into a computer folding program. All 55 clones were folded into the same structure by the Zucker folding program. The energy minimization for each RNA molecule was calculated to be −11 kcal/mol or better. The consensus structure was a stem formed between the first 10 nucleotides at the fixed 5' end and 10 of the 14 nucleotides from the conserved block with a loop that varies in size from 13 nucleotides (clone 400-23) to 23 nucleotides (clone 100-18). There is a four-base internal bulge from the 14 nucleotide block which is located in the center of the 10 base-pair stem.

EXAMPLE 4

BOUNDARY ANALYSIS AND BINDING STUDIES OF RNA TRUNCATES

Boundary Analysis

Boundary experiments were carried out in order to determine the minimum RNA structure required for binding to HIV-1 nucleocapsid protein 5' end labeled RNAs were partially alkaline hydrolyzed and fragments were then bound to nucleocapsid and passed over nitrocellulose filter. Fragments with affinities high enough to survive washes were eluted from filters and analyzed on acrylamide gels. In every case, the deletion of nucleotides from the 3' end was tolerated up to but not including the last nucleotide in the sequence block. In other words, full-length RNAs and molecules bearing sequential deletions from the 3' end were bound by nucleocapsid and retained on filters except for deletions into the conserved 14 nucleotide block. For every RNA tested, disruption of the stem between the 5' end and the nucleotides of the 3' end of the conserved block resulted in failure of the RNA fragments to bind. When the 3' end is labeled and the same hydrolysis and binding experiments are carried out, only intact RNAs were retained on filters. Thus, any deletion at the 5' end would result in failure to bind nucleocapsid.

Binding Studies of RNA Truncates

The minimum binding domain for clone 400-23 was named T-23. This RNA fragment is 37 nucleotides long beginning with the 5' end (see Table 2). In addition to this fragment, we also made a fragment where the loop was substituted with a UUCG tetra-loop resulting in a fragment which was 28 nucleotides long (BC2). Both of these fragments were synthesized on an Applied Biosystems Model 394 DNA/RNA synthesizer as well as transcribed in vitro from PCR products. Since the fragment that was determined to be the minimum required for binding had a significantly greater dissociation constant than the intact RNA, other truncates were made and their Kds were determined. The affinity of the intact 400-23 RNA (77 nucleotides) was compared with truncated molecules containing the 5' 68, 48 and 37 nucleotides. Deletion of 9 nucleotides from the 3' end (BC68) resulted in a slight reduction in affinity while deletion of 29 nucleotides (BC48) resulted in a more significant lost in affinity. Moreover, removal of an additional 11 nucleotides (T-23; minimum binding domain) caused binding to drop drastically. Although T-23 binds to nucleocapsid tighter than the parent pool (30N RNA), its dissociation constant is surprisingly greater than 400-23. All truncated RNA fragments were sequenced directly to confirm their size and sequence (data not shown). The fragment containing the tetra-loop (BC2) bound with an affinity similar to that of T-23.

EXAMPLE 5

IN VITRO INHIBITION OF ANNEALING FUNCTION

Nucleocapsid stimulates annealing of complementary oligonucleotides that are present at low concentrations. Inhibition assays were carried out to determine the extent of inhibition by 30N, 400-17 and 400-23 PaNAs. All three RNA samples were able to inhibit HIV-1 nucleocapsid protein but the two selected RNAs inhibited at concentrations which were orders of magnitude lower than that of the parent Kd pool of RNA. It took concentrations of 30N RNA at 722 nM or greater to inhibit the annealing activity of nucleocapsid in binding buffer containing 100 mM NaCl. For clone 400-17 with a Kd of $2 \times 10^{-9}$M and 400-23 with a Kd of $6 \times 10^{-9}$M the extent of inhibition was much greater. 400-17 was able to inhibit approximately 50% of the annealing activity of nucleocapsid at a concentration of 0.5 nM, whereas the $K_I$ for 400-23 was 3 nM. These results suggest that these RNAs selected against HIV-1 nucleocapsid p7 will be potent inhibitors of tRNA$^{Lys}$ annealing to the primer binding site of the HIV genome since nucleocapsid plays such a crucial role in this activity.

As the concentration of nucleocapsid present in the annealing reactions was varied, a range of nucleocapsid-dependent stimulation was observed. With a reaction time of six minutes, nearly 100% conversion of end-labeled con(+) oligonucleotide to the con± double-stranded form was observed when nucleocapsid is present in the reaction at 100 nM or greater. Nucleocapsid concentration of 10 nM resulted in about a 60% conversion while 1 nm nucleocapsid resulted in a mild increase in double-stranded DNA formation above the minus-nucleocapsid background level.

EXAMPLE 6

NUCLEOCAPSID FOOTPRINTS ON THE RNA

It was demonstrated that different parts of the RNA are shielded from digestion by S1 nuclease by varying the concentration of nucleocapsid in the reaction. There are four classes of protection from nuclease suggesting that there are at least four binding sites. At NC concentrations as low as 50 nM, sites in the conserved AACU bulge are protected from cleavage while remote nuclease-sensitive sites require up to 10M nucleocapsid to show protection. All the sites that are susceptible to the single-strand specific ribonuclease S1 are in single-stranded regions in the model. Different regions of the RNA molecule used in these experiments (400-23) show varying degrees of susceptibility to S1. Nucleocapsid footprints that are observed at high concentrations are seen both 5' and 3' of the bulge. If protein-protein interactions are important for binding to the low affinity sites this would suggest that the universally conserved 4 base bulge is a nucleation site for cooperative binding. The results are consistent with the estimated occlusion size of 7 to 8 nucleotides for HIV nucleocapsid (L. Henderson, personal communication). In addition, these results lend support to the argument for the difference in binding affinity of nucleocapsid for full-length versus the minimal binding RNA.

EXAMPLE 7

MODIFIED 2'-NH$_2$ PYRIMIDINE RNA LIGANDS TO HIV-1

Nucleocapsid

In order to generate ligands with improved stability in vitro, an experiment is carried out with randomized RNA containing amino (NH$_2$) functionalities at the 2'-position of each pyrimidine. A library of $10^{14}$ RNA molecules is generated that contains 30 nucleotides of contiguous random sequence flanked by defined sequences. Defined nucleotide sequences in the flanking regions of the template serve as primer annealing sites for PCR and the complement of the primer provides the T7 promoter sequence (a restriction site can be added for cloning). The random nucleotides of the initial candidate mixture are comprised of 2'-NH$_2$ pyrimidine bases. The rounds of selection and amplification are carried out as described supra in Examples 1–2 using art-known techniques.

TABLE 1

RNA Ligands To HIV-1 Nucleocapsid

| | SEQ ID NO: |
|---|---|
| ssDNA Template<br>5'-GCCGGATCCGGGCCTCATGTCGAA[40N]TTGAGCGTTTATTCTGAGCTCCC-3' | 1 |
| 3' PCR Primer<br>     T7 Promoter<br>5'-CCG<u>AAGCTT</u><u>AATACGACTCACTATAGGG</u>AGCTCAGAATAAACGCTCAA-3'<br>   HindIII | 2 |
| 5' PCR Primer<br>5'-GCC<u>GGATCC</u>GGGCCTCATGTCGAA-3'<br>   BamHI | 3 |

TABLE 2

RNA Ligands To HIV-1 Nucleocapsid

| Clone No. | | SEQ ID NO: |
|---|---|---|
| (400-42) | GGGAGCUCAGAAUAAACGCUCAAGAUAUGCUAACUGAGAACUCUCCCUUAGCUUCGACAUGAGGCCCGGAUCCGGC | 4 |
| (400-17) | GGGAGCUCAGAAUAAACGCUCAAGUUCUGAGAACUCUCCCAUUCUAGUGUGCUUCGACAUGAGGCCCGGAUCCGGC | 5 |
| (400-28) | GGGAGCUCAGAAUAAACGCUCAAUACCUGAGAACUCUCCCACGUAAUGUCCCUUCGACAUGAGGCCCGGAUCCGGC | 6 |
| (400-23) | GGGAGCUCAGAAUAAACGCUCAACUGAGAACUCUCCCGCUCGCAUUAUUAACCUUCGACAUGAGGCCCGGAUCCGGC | 7 |
| (400-27) | GGGAGCUCAGAAUAAACGCUCAACUGAGAACACUCCCAGUAACCUCUAUACAUUCGACAUGAGGCCCGGAUCCGGC | 8 |
| (400-15) | GGGAGCUCAGAAUAAACGCUCAAGCACACUGAGAACACUCCCUGCAACCUUACUUCGACAUGAGGCCCGGAUCCGGC | 9 |
| (400-08) | GGGAGCUCAGAAUAAACGCUCAACGAAACUAUCCUGAGAACUAUUCCCUUCUCGACAUGAGGCCCGGAUCCGGC | 10 |
| (400-25) | GGGAGCUCAGAAUAAACGCUCAAUCCUGAGAACACUCCCCAUACACAUUUUAGUUCGACAUGAGGCCCGGAUCCGGC | 11 |
| (400-31) | GGGAGCUCAGAAUAAACGCUCAAUCGCACUGAGAACUCUCCCGGUUAGCAUGCUUCGACAUGAGGCCCGGAUCCGGC | 12 |
| (400-03) | GGGAGCUCAGAAUAAACGCUCAAUCGCACUGAGAACUCUCCCGGUUAGUAUGCUUCGACAUGAGGCCCGGAUCCGGC | 13 |
| (400-22) | GGGAGCUCAGAAUAAACGCUCAAUCGCACUGAGAACUCUCCCGGUUAGUAUUCUUCGACAUGAGGCCCGGAUCCGGC | 14 |
| (400-05) | GGGAGCUCAGAAUAAACGCUCAAUCGCACUGAGAACUCUCCCGGUUAGUAUGCUUCGACAUGAGGCCCGGAUCCGGC | 15 |
| (400-44) | GGGAGCUCAGAAUAAACGCUCAAUCGCACUGAGAACUCUCCCGGUUAGUAUGCUUCGACAUGAGGCCCGGAUCCGGC | 16 |
| (400-24) | GGGAGCUCAGAAUAAACGCUCAAUAGCACUGAGAACUCUCUGGGUUAGUAUGCUUCGACAUGAGGCCCGGAUCCGGC | 17 |
| (400-19) | GGGAGCUCAGAAUAAACGCUCAAUAUAACCUGAGAACUCUCCCAUCAACCUUCGACAUGAGGCCCGGAUCCGGC | 18 |
| (400-32) | GGGAGCUCAGAAUAAACGCUCAAUAUAACCUGAGAACUCUCCCAUUAACCUUCGACAUGAGGCCCGGAUCCGGC | 19 |
| (400-36) | GGGAGCUCAGAAUAAACGCUCAAUAUAACCUGAGAACUCUCCCAUCAACCUUCGACAUGAGGCCCGGAUCCGGC | 20 |
| (400-37) | GGGAGCUCAGAAUAAACGCUCAAUAUAACCUGAGAACUCUCCCAUCCUCCAUCUUCGACAUGAGGCCCGGAUCCGGC | 21 |
| (400-34) | GGGAGCUCAGAAUAAACGCUCAAUAUAACCUGAGAACUCUCCCGAUUAGUAUGCUUCGACAUGAGGCCCGGAUCCGGC | 22 |
| (400-21) | GGGAGCUCAGAAUAAACGCUCAAACACACUGAGAACUCUCCCNGCAACCUUACUUCGACAUGAGGCCCGGAUCCGGC | 23 |
| (400-13) | GGGAGCUCAGAAUAACGCUCAAUAUAAACCUGAGAACUCUCCCAUCUGUUCCAUCUGUCGACAUUCGACAUGAGGCCCGGAUCCGGC | 24 |
| (400-12) | GGGAGCUCAGAAUAAACGCUCAAGAUACACCUGAGAACUCUCCACACGGUCCUUCGACAUGAGGCCCGGAUCCGGC | 25 |

References

Aldovini, A., and Young, R. A. (1990). Mutations of RNA and protein sequences involved in human immunodeficiency virus type 1 packaging result in production of noninfectious virus. *J. Virol.* 64, 1920–1926.

Allen, P. N., and Noller, H. F. (1989). Mutations in ribosomal proteins S4 and S12 influence the higher order structure of 16S ribosomal RNA. *J. Mol. Biol.* 203, 457–468.

Allen, P., Worland, S., and Gold, L. (1995). Isolation of high-affinity RNA ligands to HIV-1 integrase from a random pool. *Virology* 209, in press.

Barat, C., Lullien, V., Schatz, O., Keith, G., Nugeyre, M. T., Gruninger-Leitch, F., Barre-Sinoussi, F., LeGrice, S. F. J., and Darlix, J.-L. (1989). HIV-1 reverse transcriptase specifically interacts with the anticodon domain of its cognate primer tRNA. The *EMBO Jour.* 8, 3279–3285.

Bender, W., Chien, Y.-H., Chattopadhyay, S., Vogt, P. K., Gardner, M. B., and Davidson, N. (1978). High-molecular-weight RNAs of AKR, NZB, and wild mouse viruses and avian reticuloendotheliosis virus all have similar dimer structures. *J. Virol.* 25,888–896.

Bieth, E., Gabus, C., and Darlix, J.-L. (1990). A study of the dimer formation of Rous sarcoma virus RNA and of its effect on viral protein synthesis in vitro. *Nucl. Acids Res.* 18, 119–126.

Chen, H., and Gold, L. (1994). Selection of high-affinity RNA ligands to reverse transcriptase: inhibition of cDNA synthesis and RNase H activity. *Biochemistry* 33, 8746–8756.

Chen, M.-J., Garon, C. F., and Papas, T. S. (1980). Native ribonucleoprotein is an efficient transcriptional complex of avian myeloblastosis virus. *Proc. Natl. Acad. Sci. USA* 77, 1296–1300.

Coffin, J. (1982). Structure of the retroviral genome. In RNA Tumor Viruses (eds. R. Weiss, N. Teich, H. Varmus and J. Coffin). Cold Spring Harbor, N.Y. pages 261–368.

Darlix, J.-L., Zuker, M., and Spahr, P.-F. (1982). Structure-function relationship of Rous sarcoma virus leader RNA. *Nucl. Acids Res.* 10, 5183–5196.

Delahunty, M. D., South, T. L., Summers, M. F., and Karpel, R. L.(1992). Nucleic acid interactive properties of a peptide corresponding to the N-terminal zinc finger domain of HIV-1 nucleocapsid protein. *Biochemistry* 31, 6461–6469.

Dib-hajj, F. Khan, R., and Giedroc, D. P. (1993). Retroviral nucleocapsid proteins possess potent nucleic acid strand renaturation activity. *Protein Science* 2, 231–243.

Fleissner, E., and Tress, E. (1973). Isolation of a ribonucleoprotein structure from Oncornaviruses. *J. Virol.* 12, 1612–1615.

Gorelick, R. J., Nigida, Jr., S. M., Bess, Jr., J. W., Arthur, L. O., Henderson, L. E., and Rein, A. (1990). Noninfectious human immunodeficiency virus type 1 mutants deficient in genomic RNA. *J. Virol.* 64, 3207–3211.

Gorelick, R. J., Chabot, D. J., Rein, A., Henderson, L. E., and Arthur, L. O. (1993). The two zinc fingers in the human immunodeficiency virus type 1 nucleocapsid protein are not functionally equivalent. *J. Virol.* 67, 4027–4036.

Harrison, G. P., and Lever, A. M. L. (1992). The human immunodeficiency virus type 1 packaging signal and major splice donor region have a conserved stable secondary structure. *J. Virol.* 66,4144–4153.

Hostomska, Z., Matthews, D. A., Davies, J. F. II., Nodes, B. R. and Hostomsky, Z. (1991). Proteolytic release and crystallization of the RNase H domain of human immunodeficiency virus type 1 reverse transcriptase. *J. Biol. Chem.* 266, 14697–14702.

Hostomsky, Z., Appelt, K. Ogden, R. C. (1989). High-level expression of self-processed HIV-1 protease in *Escherichia coli* using asynthetic gene. *Biochem. and Biophys. Res. Comm.* 161, 1056–1063.

Julian, N., Demene, H., Morellet, N., Maigret, B., and Roques, B. P. (1993). Replacement of His[23] by Cys in a zinc finger of HIV-1 NCp7 led to a change in $^1$H NMR -E-derived 3D structure and to a loss of biological activity. *FEBS* 331, 43–48.

Kung, H.-J., Hu, S., Bender, W., Bailey, J. M., and Davidson, N. (1976). RD-114, baboon, and Woolly monkey virus PaNAs compared in size and structure. *Cell* 7, 609–620.

Lee, T. C., Sullenger, B. A., Gallardo, H. F., Ungers, G. E., and Gilboa, E. (1992). Overexpression of RRE-derived sequences inhibits HIV-1 Replication in CEM cells. *New Biol.,* 4, 66–74.

McPheeters, D. S., Stormo, G. D., and Gold, L. (1988). Autogenousregulatory site on the bacteriophage T4 gene 32 messenger RNA. *J. Mol. Biol.* 201, 517–535.

Mead, D. A., Szczesna-Skorupa, E. and Kemper, B. (1986). Single-stranded DNA 'blue' T7 promoter plasmids: a versatile tandem promoter system for cloning and protein engineering. *Prot. Eng.* 1,67–74.

Meric, C., and Spahr, P.-F. (1986). Rous sarcoma virus nucleicacid-binding protein p12 is necessary for vital 70S RNA dimer formation and packaging. *J. Virol.* 60, 450–459.

Meric, C., and Goff, S. P. (1989). Characterization of Moloneymurine leukemia virus mutants with single-aminoacid substitutions in the Cys-His box of the nucleocapsid protein. *J. Virol.* 63, 1558–1568.

Mervis, R. J., Ahmad, N., Lillehoj, E. P., Raum, M. G., Salazar, F. H. R., Chan, H. W., and Venkatesan S. (1988). The gag gene products of human immunodeficiency virus type 1: alignment within the gag open reading frame, identification of posttranslational modifications, and evidence for alternative gag precursors. *J. Virol.* 62, 3993–4002.

Morellet, N., Julian, N., De Rocquigny, H., Maigret, B., Darlix, J.-L., and Roques, B. P. (1992). Determination of the structure of the nucleocapsid protein NCp7 from the human immunodeficiency virus type 1 by $^1$H NMR. The *EMBO Jour.* 11, 3059–3065.

Murti, K. G., Bondurant, M., and Tereba, A. (1981). Secondary structural features in the 70S RNAs of Moloney murine leukemia and Rous sarcoma viruses as observed by electron microscopy. *J. Virol.* 37, 411–419.

Panganiban, A. T., and Fiore, D. (1988). Ordered interstrand and intrastrand DNA transfer during reverse transcription. *Science* 241, 1064–1069.

Prats, A. C., Sarih, L., Gabus, C., Lityak, S., Keith, G., and Darlix, J.-L. (1988). Small finger protein of avian and murine retroviruses has nucleic acid annealing activity and positions the replication primer tRNA onto genomic RNA. *The EMBO Jour.* 7,1777–1783.

Ratner, L., Haseltine, W., Patarca, R., Livak, K. J., Starcich, B., Josephs, S. F., Doran, E. R., Fafalski, J. A., Whitehorn, E. A., Baumeister, K., Ivanoff, L., Petteway, S. R. Jr., Pearson, M. L., Lautenberger, J. A., Papas, T. S., Ghrayeb, J., Chang, N. T., Gallo, R. C. and Wong-Staal, F. (1985). Complete nucleotide sequence of the AIDS virus, HTLV-III. *Nature* 313, 277–284.

South, T. L., and Summers, M. F. (1993). Zinc- and sequence-dependent binding to nucleic acids by the N-terminal zinc finger of the HIV-1 nucleocapsid protein:

NMR structure of the complete with the Psi-site analog, dACGCC. *Protein Science* 2, 3–19.

Stern, S., Moazed, D., and Noller, H. F. (1988). Structural Analysis of RNA Using Chemical and enzymatic probing monitored by primer extension. *Meth. Enzymol.* 164, 481–489.

Sullenger, B. A., Gallardo, H. F., Ungers, G. E., and Gilboa, E.(1990). Overexpression of TAR sequences renders cells resistant to human immunodeficiency virus replication. *Cell* 63, 601–608.

Sullenger, B. A., Gallardo, H. F., Ungers, G. E., and Gilboa, E. (1991). Analysis of trans-acting response decoy RNA-mediated inhibition of human immunodeficiency virus type 1 transactivation. *J. Virol.* 65, 6811–6816.

Surovoy, A., Dannull, J., Moelling, K., and Jung, G. (1993). Conformational and nucleic acid binding studies on the synthetic nucleocapsid protein of HIV-1. *J. Mol. Biol.* 229, 94–104.

Tuerk, C., and Gold, L. (1990). Systematic evolution of ligands by exponential enrichment: RNA ligands to bacteriophage T4 DNA polymerase. *Science* 249, 505–510.

Tuerk, C., Eddy, S., Parma, D., and Gold, L. (1990). Autogenous translational operator recognized by bacteriophage T4 DNA polymerase. *J. Mol. Biol.* 249, 749–761.

Vaishnav, Y. N., and Wong-Staal, F. (1991) The biochemistry of AIDS. *Annu. Rev. Biochem.* 60, 577–630.

Varmus, H., and Brown, P. (1989). Retroviruses. In Mobile DNA (eds. D. E. Berg and M. M. Howe). Cold Spring Harbor Laboratory, New York pages 53–108.

Wain-Hobson, S. (1994). Is antigenic variation of HIV important for AIDS and what might be expected in the future?

In The Evolutionary Biology of Viruses. (ed. S. S. Morse). Raven Press. New York pages 185–209.

Weiss, S., König, B., Morikawa, Y., and Jones, I. (1992). Recombinant HIV-1 nucleocapsid protein p15 produced as a fusion protein with glutathione S-transferase in *Escherichia coli* mediates dimerization and enhances reverse transcription of retroviral RNA. *Gene* 121, 203–212.

Wong-Staal, F. (1990). Human immunodeficiency viruses and their replication. In Virology. $2^{nd}$ Edition (eds. B. N. Fields, D. M. Knipe, et al.). Raven Press. New York pages 1529–1540.

---

We claim:

1. A method for identifying nucleic acid ligands to nucleocapsid comprising:

a) preparing a candidate mixture of nucleic acids;

b) contacting the candidate mixture of nucleic acids with nucleocapsid, wherein nucleic acids having an increased affinity to nucleocapsid relative to the candidate mixture may by partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acid sequences with relatively higher affinity and specificity for binding to nucleocapsid, whereby nucleic acid ligands of nucleocapsid may be identified.

2. The method of claim 1 further comprising:
   e) repeating steps b), c), and d).

3. The method of claim 1, wherein the candidate mixture contacted includes non-amplifiable random pool nucleic acids.

4. The method of claim 1 wherein said candidate mixture of nucleic acids is comprised of single stranded nucleic acids.

5. The method of claim 4 wherein said single stranded nucleic acids are ribonucleic acids.

6. The method of claim 4 wherein said single stranded nucleic acids are deoxyribonucleic acids.

7. The method of claim 5 wherein said candidate mixture of nucleic acids comprises 2'-amino (2'-NH$_2$) modified ribonucleic acids.

8. The method of claim 1 wherein said nucleocapsid is HIV-1 nucleocapsid.

* * * * *

SEQUENCE LISTING ( 1 ) GENERAL INFORMATION:

( i i i ) NUMBER OF SEQUENCES: 29

( 2 ) INFORMATION FOR SEQ ID NO: 1:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 1:

```
GCCGGATCCG GGCCTCATGT CGAANNNNNN NNNNNNNNNN NNNNNNNNNN      50
NNNNNNNNNN NNNNTTGAGC GTTTATTCTG AGCTCCC                    87
```

( 2 ) INFORMATION FOR SEQ ID NO: 2:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 2:

```
CCGAAGCTTA ATACGACTCA CTATAGGGAG CTCAGAATAA ACGCTCAA        48
```

( 2 ) INFORMATION FOR SEQ ID NO: 3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 3:

```
GCCGGATCCG GGCCTCATGT CGAA                                  24
```

( 2 ) INFORMATION FOR SEQ ID NO: 4:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 4:

```
GGGAGCUCAG AAUAAACGCU CAAGAUAUGC UAACUGAGAA CUCUCCCCUU    50
AGCUUCGACA UGAGGCCCGG AUCCGGC                            77
```

(2) INFORMATION FOR SEQ ID NO: 5:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 5:

```
GGGAGCUCAG AAUAAACGCU CAAGUUCUGA GAACUCUCCC CAUUCUAGUG    50
UGCUUCGACA UGAGGCCCGG AUCCGGC                            77
```

(2) INFORMATION FOR SEQ ID NO: 6:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 6:

```
GGGAGCUCAG AAUAAACGCU CAAUACCUGA GAACUCUCCC ACGUAAUGUC    50
CCCUUCGACA UGAGGCCCGG AUCCGGC                            77
```

(2) INFORMATION FOR SEQ ID NO: 7:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 7:

```
GGGAGCUCAG AAUAAACGCU CAACUGAGAA CUCUCCCGCU CGCAUUAUUA    50
ACCUUCGACA UGAGGCCCGG AUCCGGC                            77
```

(2) INFORMATION FOR SEQ ID NO: 8:

(i) SEQUENCE CHARACTERISTICS:
    (A) LENGTH: 76 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 8:

```
GGGAGCUCAG AAUAAACGCU CAACUGAGAA CACUCCAGU AACCUCUAUA     50
CAUUCGACAU GAGGCCCGGA UCCGGC                             76
```

(2) INFORMATION FOR SEQ ID NO: 9:

(i) SEQUENCE CHARACTERISTICS:
    (A) LENGTH: 77 base pairs
    (B) TYPE: nucleic acid
    (C) STRANDEDNESS: single
    (D) TOPOLOGY: linear (ii) MOLECULE TYPE: RNA (xi) SEQUENCE DESCRIPTION: SEQ ID NO: 9:

```
GGGAGCUCAG AAUAAACGCU CAAGCACACU GAGAACACUC CCUGCAACCU    50
```

```
                 UACUUCGACA UGAGGCCCGG AUCCGGC                                    77
```

( 2 ) INFORMATION FOR SEQ ID NO: 10:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 10:

```
                 GGGAGCUCAG AAUAAACGCU CAACGAAACU AUCCUGAGAA CUCUCCCUUC           50
                 UCCUUCGACA UGAGGCCCGG AUCCGGC                                    77
```

( 2 ) INFORMATION FOR SEQ ID NO: 11:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 11:

```
                 GGGAGCUCAG AAUAAACGCU CAAUCCUGAG AACACUCCCC AUACACAUUU           50
                 UAGUUCGACA UGAGGCCCGG AUCCGGC                                    77
```

( 2 ) INFORMATION FOR SEQ ID NO: 12:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 12:

```
                 GGGAGCUCAG AAUAAACGCU CAAUCGCACU GAGAACUCUC CCGGUUAGCA           50
                 UGCUUCGACA UGAGGCCCGG AUCCGGC                                    77
```

( 2 ) INFORMATION FOR SEQ ID NO: 13:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 13:

```
                 GGGAGCUCAG AAUAAACGCU CAAUCGCACU GAGAACUCUC CCGGUUAGUA           50
                 UGCUUCGACA UGAGGCCCGG AUCCGGC                                    77
```

( 2 ) INFORMATION FOR SEQ ID NO: 14:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 14:

```
                 GGGAGCUCAG AAUAAACGCU CAAUCGCACU GAGAACUCUC CCGGUUAGUA           50
                 UUCUUCGACA UGAGGCCCGG AUCCGGC                                    77
```

( 2 ) INFORMATION FOR SEQ ID NO: 15:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 15:
```
GGGAGCUCAG AAUAAACGCU CAAUCACACU GAGAACUCUC CCGGUUAGUA      50
UGCUUCGACA UGAGGCCCGG AUCCGGC                              77
```

( 2 ) INFORMATION FOR SEQ ID NO: 16:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 16:
```
GGGAGCUCAG AAUAAACGCU CAAUCGCACU GAGAACUCUC CCGGUUAGUA      50
UGCUUCGACA UGAGGCCCGG AUCCGGC                              77
```

( 2 ) INFORMATION FOR SEQ ID NO: 17:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 17:
```
GGGAGCUCAG AAUAAACGCU CAAUAGCACU GAGAACUCUC CUGGUUAGUA      50
UGCUUCGACA UGAGGCCCGG AUCCGGC                              77
```

( 2 ) INFORMATION FOR SEQ ID NO: 18:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 18:
```
GGGAGCUCAG AAUAAACGCU CAAUAUAACC UGAGAACUCU CCCUCCAAUU      50
AACCUUCGAC AUGAGGCCCG GAUCCGGC                             78
```

( 2 ) INFORMATION FOR SEQ ID NO: 19:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 19:
```
GGGAGCUCAG AAUAAACGCU CAAUAUAACC UGAGAACUCU CCCUCCAUUA      50
ACCUUCGACA UGAGGCCCGG AUCCGGC                              77
```

( 2 ) INFORMATION FOR SEQ ID NO: 20:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO: 20:
```
GGGAGCUCAG AAUAAACGCU CAAUAUAACC UGAGAACUCU CCCUCCAUCA      50
ACCUUCGACA UGAGGCCCGG AUCCGGC                              77
```

( 2 ) INFORMATION FOR SEQ ID NO: 21:

( i ) SEQUENCE CHARACTERISTICS:
        ( A ) LENGTH: 77 base pairs

29

-continued ( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 21:

```
GGGAGCUCAG AAUAAACGCU CAAUAUAACC UGAGAACUCU CCCUCCAUCU      50
UCCUUCGACA UGAGGCCCGG AUCCGGC                              77
```

( 2 ) INFORMATION FOR SEQ ID NO: 22:

( i ) SEQUENCE CHARACTERISTICS:
( A ) LENGTH: 78 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 22:

```
GGGAGCUCAG AAUAAACGCU CAAUAUAACC UGAGAACUCU CCCGAUUAGU      50
AUGCUUCGAC AUGAGGCCCG GAUCCGGC                             78
```

( 2 ) INFORMATION FOR SEQ ID NO: 23:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 23:

```
GGGAGCUCAG AAUAAACGCU CAAACACACU GAGAACACUC CCNGCAACCU      50
UACUUCGACA UGAGGCCCGG AUCCGGC                              77
```

( 2 ) INFORMATION FOR SEQ ID NO: 24:

( i ) SEQUENCE CHARACTERISTICS:
( A ) LENGTH: 82 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 24:

```
GGGAGCUCAG AAUAAACGCU CAAUAUAACC UGAGAACUCU CCCAUCUGUU      50
CCAUGUUCUU CGACAUGAGG CCCGGAUCCG GC                        82
```

( 2 ) INFORMATION FOR SEQ ID NO: 25:

( i ) SEQUENCE CHARACTERISTICS:
( A ) LENGTH: 77 base pairs
( B ) TYPE: nucleic acid
( C ) STRANDEDNESS: single
( D ) TOPOLOGY: linear ( i i ) MOLECULE TYPE: RNA ( x i ) SEQUENCE DESCRIPTION: SEQ ID NO: 25:

```
GGGAGCUCAG AAUAAACGCU CAAGAUACAC CUGAGAACUC UCCCACACGG      50
UCCUUCGACA UGAGGCCCGG AUCCGGC                              77
```

( 2 ) INFORMATION FOR SEQ ID NO: 26:

( i ) SEQUENCE CHARACTERISTICS:
( A ) LENGTH: 14 amino acids
( B ) TYPE: amino acid
( D ) TOPOLOGY: linear ( i i ) MOLECULE TYPE: protein ( x i ) SEQUENCE DESCRIPTION: SEQ ID NO: 26:

```
Cys Xaa Xaa Cys Xaa Xaa Xaa Xaa His Xaa Xaa Xaa Xaa Cys    14
```

( 2 ) INFORMATION FOR SEQ ID NO: 27:

(i) SEQUENCE CHARACTERISTICS:
   (A) LENGTH: 25 base pairs
   (B) TYPE: nucleic acid
   (C) STRANDEDNESS: single
   (D) TOPOLOGY: linear (ii) MOLECULE TYPE: DNA (xi) SEQUENCE DESCRIPTION: SEQ ID NO: 27:
   CCCGGATCCT CTTTACCTCT GTGTG                     25

(2) INFORMATION FOR SEQ ID NO: 28:

(i) SEQUENCE CHARACTERISTICS:
   (A) LENGTH: 49 base pairs
   (B) TYPE: nucleic acid
   (C) STRANDEDNESS: single
   (D) TOPOLOGY: linear (ii) MOLECULE TYPE: DNA (xi) SEQUENCE DESCRIPTION: SEQ ID NO: 28:
   CCGAAGCTTA ATACGACTCA CTATAGGGAC TATTGATGGC CTTCCGACC     49

(2) INFORMATION FOR SEQ ID NO: 29:

(i) SEQUENCE CHARACTERISTICS:
   (A) LENGTH: 40 base pairs
   (B) TYPE: nucleic acid
   (C) STRANDEDNESS: single
   (D) TOPOLOGY: linear (ii) MOLECULE TYPE: DNA (xi) SEQUENCE DESCRIPTION: SEQ ID NO: 29:
   CAATGACCGC ATGGGATCCG TGTGGAAAAT CTCTAGCAGT           40